United States Patent
Parrini et al.

[11] Patent Number: 5,880,438
[45] Date of Patent: Mar. 9, 1999

[54] STEAM STERILIZATION APPARATUS AND CONTROL SYSTEM

[75] Inventors: Mark J. Parrini, Erie; David F. McCall, Edinboro; Francis J. Zelina, Lake City; Terrence L. Lukas, Erie, all of Pa.

[73] Assignee: Steris Corporation, Mentor, Ohio

[21] Appl. No.: 832,648

[22] Filed: Apr. 4, 1997

[51] Int. Cl.[6] .................................................. H05B 1/02
[52] U.S. Cl. ........................... 219/519; 219/481; 219/506; 219/518; 219/496; 422/105; 392/324; 392/386
[58] Field of Search .................................. 219/481, 506, 219/518, 496, 519, 497, 505, 501, 502; 392/404, 324–333, 387, 386, 451, 464; 122/448.1; 422/105

[56] References Cited

U.S. PATENT DOCUMENTS

| 5,064,998 | 11/1991 | Holling | 219/519 |
| 5,283,421 | 2/1994 | Richards | 219/519 |
| 5,585,025 | 12/1996 | Idland | 219/497 |
| 5,616,265 | 4/1997 | Altman | 219/497 |
| 5,692,096 | 11/1997 | Massey et al. | 392/464 |
| 5,739,504 | 4/1998 | Lyons et al. | 219/494 |
| 5,758,018 | 5/1998 | Fowler, Jr. | 392/402 |

FOREIGN PATENT DOCUMENTS

WO/96/41099 5/1996 WIPO.

Primary Examiner—Mark H. Paschall
Attorney, Agent, or Firm—Fay, Sharpe, Beall, Fagan, Minnich & McKee

[57] ABSTRACT

A steam sterilization apparatus (10) includes an electronic control system having a main control circuit (C) including a central processing unit (68), an input device (36), and output devices (24,28) provided on a single circuit board (22) which is attached to a front bezel (16) of the sterilizer (10). The sterilizer (10) includes a flash steam generator (56). The main control circuit (C) implements an over-temperature feedback circuit (160) that disconnects the heating elements (162) in the steam generator (56) from electrical power when an over-temperature condition is detected. Isolated feedback is provided to the central processing unit (68) confirming the heating element disconnection operation. The control system includes error switches (82, 86, 88) that detect various error conditions. Upon an error condition being detected, the steam supply to the steam sterilization chamber (12) and/or to the pressurized steam seal (42) of the apparatus (10) is halted. The main control circuit (C) implements a feedback circuit (150) confirming the steam shutdown procedure. The main control circuit (C) also includes a ratiometric analog input circuit (74) that eliminates temperature drift in analog measurements.

17 Claims, 7 Drawing Sheets

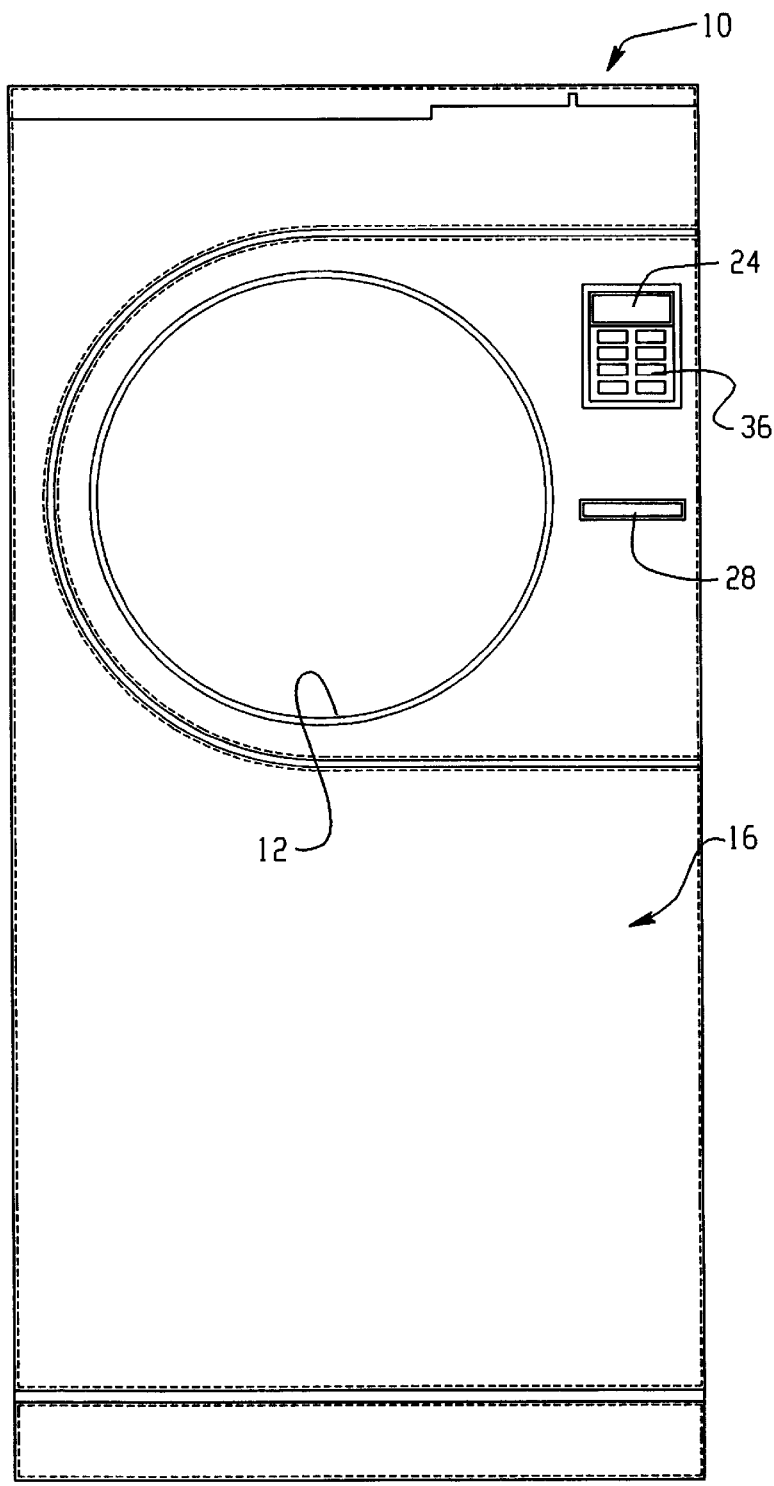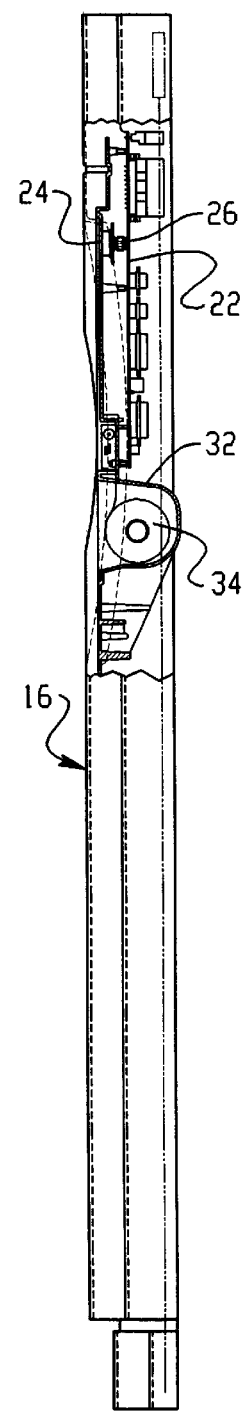
Fig. 1
Fig. 2

STEAM STERILIZATION APPARATUS AND CONTROL SYSTEM

BACKGROUND OF THE INVENTION

The present invention relates to the disinfecting and sterilizing arts. It finds particular application in conjunction with compact steam sterilization systems used in hospitals, clinics, physicians offices, and other healthcare facilities as well as those used in pharmaceutical, laboratory, and other facilities.

Steam sterilizers are highly effective in sterilizing medical instruments and related items that are able to withstand the high temperature, high moisture, and high pressure within the steam sterilization chamber. Despite the effectiveness and popularity of steam sterilizers, the control systems for these devices have remained relatively large, non-integrated, and expensive. For example, a keypad for user input, a printer for hard copy output, and a visual display were connected to multiple circuit "cards" or boards that drive these input and output devices. The input and output boards were also connected with the main controller circuit board. These connections were provided through wiring harnesses and the like that increased the size of the control system and the sterilizer overall, increased material and assembly costs, and increased the number of electrical connections in the control system which led to unreliability.

Furthermore, typical compact steam sterilizer control systems have not included feedback systems to provide an added level of safety and effectiveness by ensuring that, when the controller initiated an operation; the operation was actually carried out. With prior systems, the controller could be unaware that a relay has failed in an open or closed position. The controller might energize or deenergize a relay coil without any actual relay operation being carried out. This could result in erroneous machine operations and, in certain instances, could result in an operator of the sterilizer being subjected to a dangerous condition.

Another drawback associated with prior steam sterilizer control systems was their lack of ratiometric circuitry. The high temperature within and surrounding known steam sterilizers caused the output signals from analog devices to drift. An analog-to-digital converter received a varying analog input signal from a pressure or temperature sensor and provided varying output data to the central processing unit of the control system depending upon the temperature of the sensor and the associated circuitry. With non-ratiometric control systems, one could not be entirely certain of pressure, temperature, and other analog measurements that are critical to effective and safe sterilizer performance.

Prior steam sterilizers utilized common tap water for steam generation in a boiler or the like. Commonly assigned and co-pending U.S. patent application entitled Steam Delivery System for a Decontamination Apparatus, filed on even date herewith and expressly incorporated by reference herein, describes a flash steam generator system for generating steam as an alternative to using a boiler. However, the flash generator uses filtered water to prevent fouling of the flash generator due to mineral deposits and the like. Prior control systems for steam sterilizers did not control the delivery of filtered water to a flash steam generator. Furthermore, prior control systems did not inform an operator when a water filter was due for replacement.

The present invention provides a new and improved method and apparatus for overcoming the above-referenced problems and others.

SUMMARY OF THE INVENTION

In accordance with one aspect of the present invention, a steam sterilizer includes a steam chamber and a steam generator. The steam generator has a steam output in selective fluid communication with the steam chamber and includes at least one heating element selectively connected to an electrical heating element power source. An electronic control system includes a central processing unit. An over-temperature switch is positioned to sense the temperature of the steam generator. The sterilizer includes means for disconnecting the one or more heating elements from the electrical heating element power source in response to a change of state in the over-temperature switch which indicates an over-temperature condition in the steam generator. A feedback circuit provides feedback to the central processing unit in response to a change of state of the over-temperature switch.

In accordance with another aspect of the present invention, a steam sterilization apparatus includes a generally hollow steam chamber, a door providing selective access to the steam chamber, and means for generating steam. At least one steam valve selectively connects an output of the steam generating means in fluid communication with at least the steam chamber. An electronic controller is connected to and controls the opening and closing of the steam valve. At least one relay is controllable by the electronic controller and has an "on" state connecting the steam valve to a source of electrical power and an "off" state disconnecting the steam valve from a source of electrical power. The sterilizer further includes means for providing a feedback signal to the electronic controller based upon the state of the at least one relay. The first state of the feedback signal corresponds to the "on" state of the at least one relay and the second state of the feedback signal corresponds to the "off" state of the at least one relay.

In accordance with another aspect of the present invention, a sterilization apparatus includes a generally hollow steam chamber and at least one analog pressure sensor for sensing pressure in the chamber. The apparatus also includes at least one analog temperature sensor for sensing temperature in the chamber. An analog input circuit of the apparatus includes an analog-to-digital converter and a selector circuit for selectively establishing a ratiometric input circuit including one of the temperature and pressure sensors. The analog circuit also includes a multiplexing circuit for selectively connecting the selected one of the ratiometric input circuits to an input of the analog-to-digital converter.

One advantage of the present invention is that it is effective and easy to operate.

Another advantage of the present invention is that it safely and accurately controls the sterilization process.

Still another advantage of the present invention is that it provides a real time feedback of actual monitored system parameters.

Yet another advantage of the present invention is that it simplifies manufacture and maintenance.

A further advantage of the present invention is that it minimizes temperature drift of analog input signals.

A further advantage of the present invention is that it assures optimal operation by providing a water filter monitoring system that notifies an operator of the need for filter replacement.

Still further advantages of the present invention will become apparent to those of ordinary skill in the art upon reading and understanding the following detailed description of the preferred embodiment.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

FIG. 1 is a front elevational view of a steam sterilization apparatus in accordance with the present invention;

FIG. 2 is a side elevational view, in partial section, of the front panel of the steam sterilization apparatus of FIG. 1;

DETAILED DESCRIPTION OF THE PREFERRED EMBODIMENT

Figure 3:
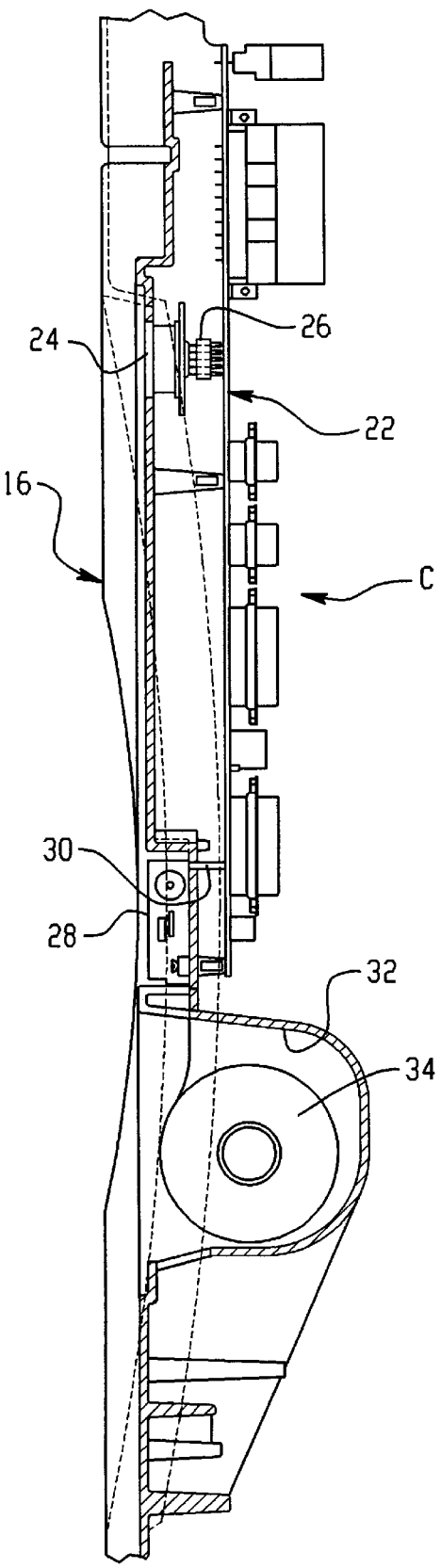
FIG. 3 is an enlarged partial side view in cross section of the front panel shown in FIG. 2, more clearly showing a control system in accordance with the present invention.

With particular reference to FIGS. 1–4, a steam sterilization apparatus 10 has a high pressure steam chamber 12 into which items to be sterilized are placed on racks or in trays. A door 14 slides or otherwise moves into position to selectively seal the chamber 12 during sterilization operations. Once the chamber 12 is sealed with the door 14, high pressure steam is introduced into the chamber 12 to sterilize the items located therein.

The sterilizer 10 includes a front panel or bezel 16. A control system includes a main control circuit C mounted on a circuit board 22 which is fastened directly to the bezel 16. The circuit C includes a visual display 24 such as a vacuum fluorescent display (VFD), a cathode ray tube (CRT) display, a liquid crystal display (LCD), or a light emitting diode (LED) display. The display 24 is connected directly to the circuit board 22 using an electrical connector 26 such as a header connector or the like having male pins projecting from one of the board 22 and the display 24 and having female sockets located on the other of the board 22 and display 24. The display 24 provides an operator of the apparatus 10 with visual information regarding the status of the sterilization cycle being executed.

The main control circuit C also includes a printer 28 which connects directly to the main circuit board 22 using an electrical connector 30 such as a header connector described above. A paper well 32 is defined in the bezel 16 and includes a roll of printer paper 34. The printer 28 prints sterilization process information regarding one or more sterilization cycles on the paper 34 to provide a permanent hard copy record to the operator of the apparatus 10. The main control circuit C also includes one or more input devices for operator control of the apparatus 10 and for operator input of sterilization process parameters. Specifically, the circuit board 22 of the control system includes an input device 36 such as a keyboard, a key pad, a touch screen, or the like connected directly thereto using one or more electrical connectors as described above.

Figure 4:
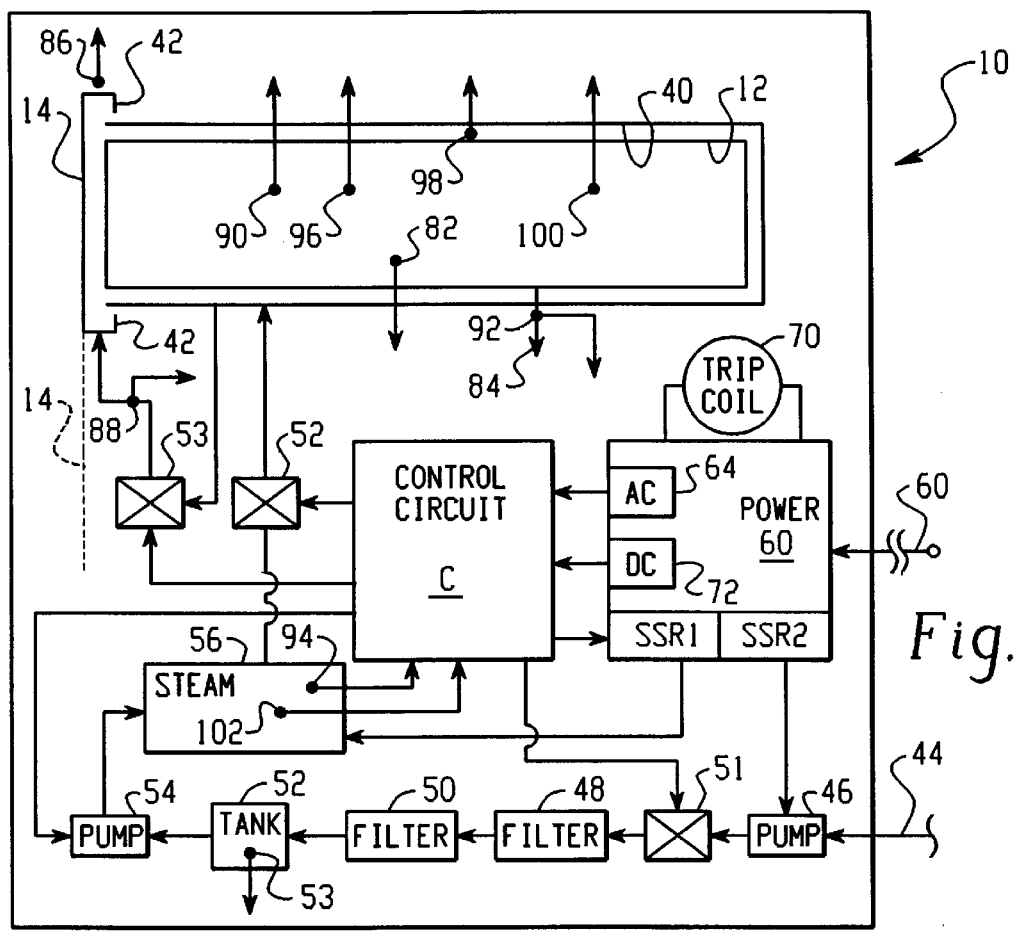
FIG. 4 is a schematic illustration of a steam sterilization apparatus in accordance with the present invention.

With reference particularly to FIG. 4, the steam sterilization apparatus 10 in accordance with the present invention is shown diagrammatically. The steam chamber 12 is surrounded by a steam jacket 40. Steam fills the annular space between the chamber 12 and the jacket 40 such that the chamber 12 is evenly heated. The door 14 selectively seals the chamber 12 during sterilization operations. When the door 14 is closed and sealed, a high pressure or a vacuum condition can be maintained in the chamber 12. The door 14 can be a radial arm door which includes a plurality of radial arms that engage the chamber 12 and maintain a pressure seal. However, the present invention preferably includes door 14 that slides between an open position (shown in phantom) and a closed position. An active seal 42 surrounds the door 14 and is selectively pressurized with steam when the door 14 is closed to form a pressure-tight seal between the door 14 and the chamber 12.

The steam sterilization apparatus 10 is connected to a source of water 44, which is generally tap water. The water from the source 44 is boiled to generate steam. Known steam sterilizers utilize a boiler or like means for steam generation, and such can also be used in conjunction with the sterilizer 10. However, the sterilizer 10 preferably includes a flash steam generator system as described in the copending and commonly assigned U.S. patent application entitled Steam Delivery System for a Decontamination Apparatus filed on even date herewith and expressly incorporated by reference herein. Specifically, water from the source 44 is pumped by a pump 46 at a high pressure, such as 100 pounds per square inch (psi), to a pre-filter 48 which filters sediment and other relatively large particulates from the water. A solenoid valve S2 selectively connects the pump 46 in fluid communication with the pre-filter 48. A second filter 50, which is a reverse osmosis filter or the like, further filters impurities from the incoming water. The second filter 50 is connected to a holding tank 52 which is filled with filtered water that is used for steam generation. When steam is needed, a metering pump 54 supplies a precise amount of water from the tank 52 to a heated flash steam generator block 56. Water introduced into the heated block 56 quickly turns to steam which is "flashed" off. The block 56 outputs steam to the steam jacket 40 and the chamber 12 through a steam chamber valve S2. Steam from the block 56 is also selectively communicated to the active door seal 42 by way of the jacket 40 through an active seal valve S3 to pressurize the seal 42. The valves S2,S3, which can be provided by solenoid valves or the like, are selectively opened by the main control circuit C to allow the passage of steam therethrough to the chamber 12 and the seal 42, respectively.

Figure 5:
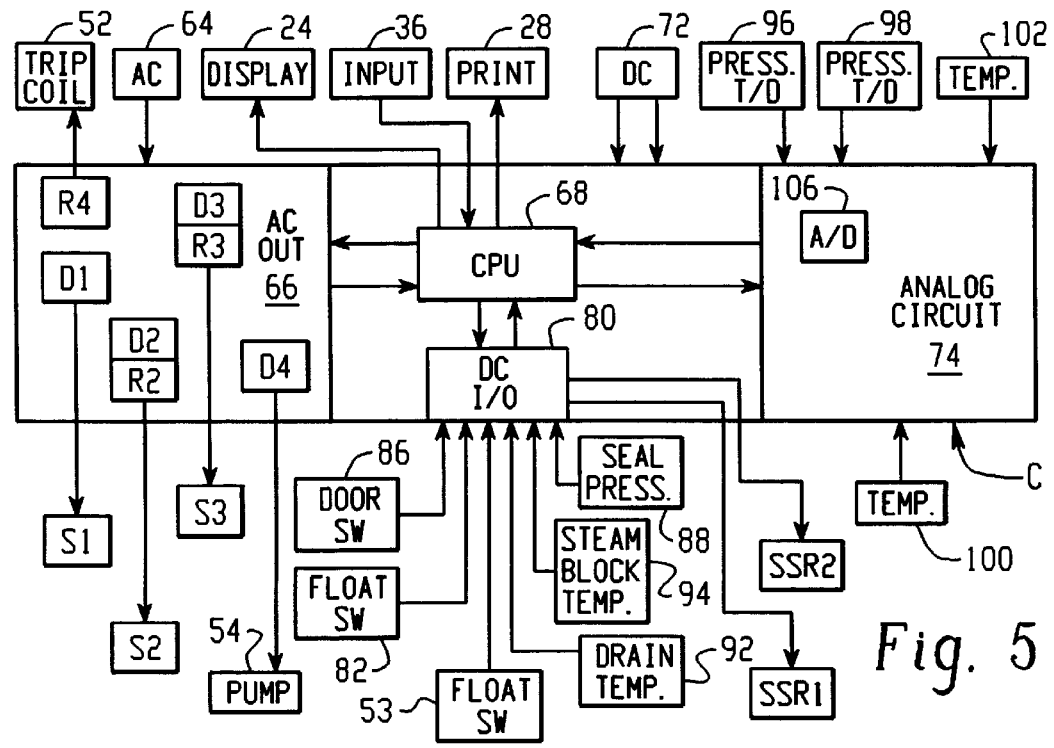
FIG. 5 is a schematic illustration of a steam sterilization apparatus control system in accordance with the present invention.

With reference now also to FIG. 5, the steam sterilization apparatus control system includes the main control circuit C which, in addition to controlling the user input and output devices 24,28,36 described above, also controls the execution of one or more steam sterilization cycles of the apparatus 10. The apparatus 10 includes a power box 60 which is connected to and supplied with electrical power from a standard electrical utility connection 62 such as 240 volts A.C. (VAC), single-phase, 50–60 Hertz (Hz) or the like. The power box 60 provides all of the needed electrical power to the apparatus 10.

FIG. 5 individually shows the major components housed within the power box 60 and their relationship to the remainder of the control system. The power box 60 includes an AC output 64 which provides AC power to an AC output driver circuit 66 of the control circuit C. The AC output driver circuit 66 includes a plurality of AC output drivers D1,D2,D3 which are controlled by a central processing unit (CPU) 68, which can be any suitable electronic controller, to selectively energize the solenoid valves S1,S2,S3, respectively. An AC output driver D4 provides AC output power to the metering pump 54 that selectively injects water into the steam generation block 56.

As is described in detail below, the AC output driver circuit 66 implements a switched neutral feedback circuit that ensures no steam is delivered to the chamber 12 or to the seal 42 when an error condition has been detected—e.g., when the door 14 is not closed, when water has accumulated in the chamber 12, when the seal 42 is not intact, or when any other similar error condition occurs. Specifically, the switched neutral feedback circuit includes relays R2,R3 that selectively disconnect the AC power connection from the solenoid valves S2,S3 to deenergize the valves S2,S3. Preferably, the relays R2,R3 selectively disconnect the neutral AC power connection, although the AC hot connection may alternatively be disconnected. The AC output section 66 of the circuit C also implements an over-temperature feedback circuit described below which includes a relay R4 that selectively completes a circuit to energize a main trip coil 70 or similar means in the power box 60 to interrupt all power to the heating elements in the steam generator block 56 for safety reasons, for example, when the steam block 56 overheats. The main trip coil 70 also acts as a standard circuit breaker to break the circuit if the heating elements draw excessive current.

As is further shown in FIGS. 4 and 5, the power box 60 also includes a DC power supply 72 that is connected to and supplies DC electrical power to the main control circuit C. Specifically, the DC power supply 72 supplies DC power to the central processing unit (CPU) 68 and to an analog section 74 of the main circuit C. A circuit breaker (not shown) is preferably provided in the power box 60 between the DC power supply 72 and the circuit C.

The power box 60 also includes relays which are preferably solid state relays SSR1,SSR2 that selectively deliver power to the high pressure water pump 46 and the heating elements (not shown) in the steam generation block 56. The high pressure water pump 46 and the heating elements in the steam generation block 56 are alternatively powered through the AC driver output circuit 66 of the circuit C. The solid state relays SSR1,SSR2 are connected to a DC input/output circuit 80. The DC input/output circuit 80 provides an interface between the CPU 68 and DC elements external to the circuit C. The CPU 68 selectively turns the relays SSR1,SSR2 "on" and "off" to selectively energize and deenergize the pump 46 and the heating elements in the block 56, respectively.

The control system of the steam sterilizer apparatus 10 includes a plurality of sensors and switches that monitor various aspects of the apparatus 10 and provide input data to the main control circuit C. Referring again to FIG. 4, the chamber 12 includes a float switch 82 that changes state if water accumulates in the chamber 12. The existence of water in the chamber 12 indicates a system error with the steam generation system or with the drain 84. If water is present in the chamber 12, the sterilizer 10 will not be effective and an operator could be burned upon opening the door 14. Therefore, the steam to chamber valve S2 must be disabled if the float switch 82 senses water in the chamber 12. A second float switch 53 is present in the filtered water tank 52 to monitor the water level in the tank 52. The float switch 53 allows the CPU 68 to control the operation of the high pressure pump 46 and the water input valve S1 such that water evacuated from the tank 52 for steam generation is replenished.

A switch 86, such as a proximity switch or the like, senses whether or not the door 14 is properly closed to seal the chamber 12. Unless the switch 86 senses the door 14 in the closed position, the seal steam valve S3 is not opened. This prevents the accidental discharge of hot steam onto an operator when the door 14 is open. Also, a seal pressure switch 88 senses whether or not the active seal 42 is pressurized. If the seal 42 does not properly pressurize, the valve S2 is not opened. This prevents the escape of hot steam between the chamber 12 and the door 14 which can burn an operator. A defective seal 42 can also prevent the desired high pressure steam atmosphere from being established within the chamber 12 for sterilization operations. A pressure safety switch 90 operates independently of the control circuit C to illuminate a warning light (not shown) that informs an operator of the existence of pressure in the chamber 12.

Temperature switches 92,94, such as bi-metal switches or the like, are positioned to sense the temperature in the chamber drain 84 and the temperature of the steam generation block 56, respectively. The switch 92 senses an excessive temperature in the drain 84 which could melt or damage plastic drain conduits. If excessive heat is detected in the drain 84, cold water is automatically added thereto to prevent damage. Likewise, the switch 94 senses excessive temperature in the steam generation block 56 which could damage the block 56. If excessive heat is detected in the block 56, the heating elements in the block 56 are deenergized as is described in detail below.

The control system also includes a plurality of analog sensors for temperature and pressure measurement. Pressure transducers 96,98 provide information to the main control circuit C regarding the pressure in the chamber 12 and the pressure in the steam jacket 40, respectively. The pressure data provides the control circuit C with information regarding the sterilization process. One or more temperature sensors 100, such as a single or dual element resistance temperature detector (RTD) senses the temperature within the chamber 12 and provides temperature data to the control circuit C. In addition to the bi-metal switch 94, the steam generation block 56 also includes an analog temperature sensor 102, such as an RTD, to provide an input signals to the control circuit C regarding the temperature of the steam generation block 56.

FIG. 5 shows the relationship between the sensors of the control system and the main control circuit C. The filtered water tank float switch 53, the steam chamber float switch 82, the door switch 86, the seal pressure switch 88, the drain temperature switch 92 and the steam generator block temperature switch 94 are connected to the DC input/output section 80 of the circuit C such that the CPU 68 can determine whether the switches 82,86,88,92,94 are opened or closed and operate the apparatus 10 accordingly.

The analog sensors including the chamber pressure transducer 96, the steam jacket pressure transducer 98, the chamber temperature sensor 100, and the steam generation block temperature sensor 102 connect to the analog section 74 of the circuit C. The analog section 74 includes an analog-to-digital converter 106 that converts the analog signals from the sensors 96,98,100,102 into digital data and transmits the digital data to the CPU 68.

Figure 6:
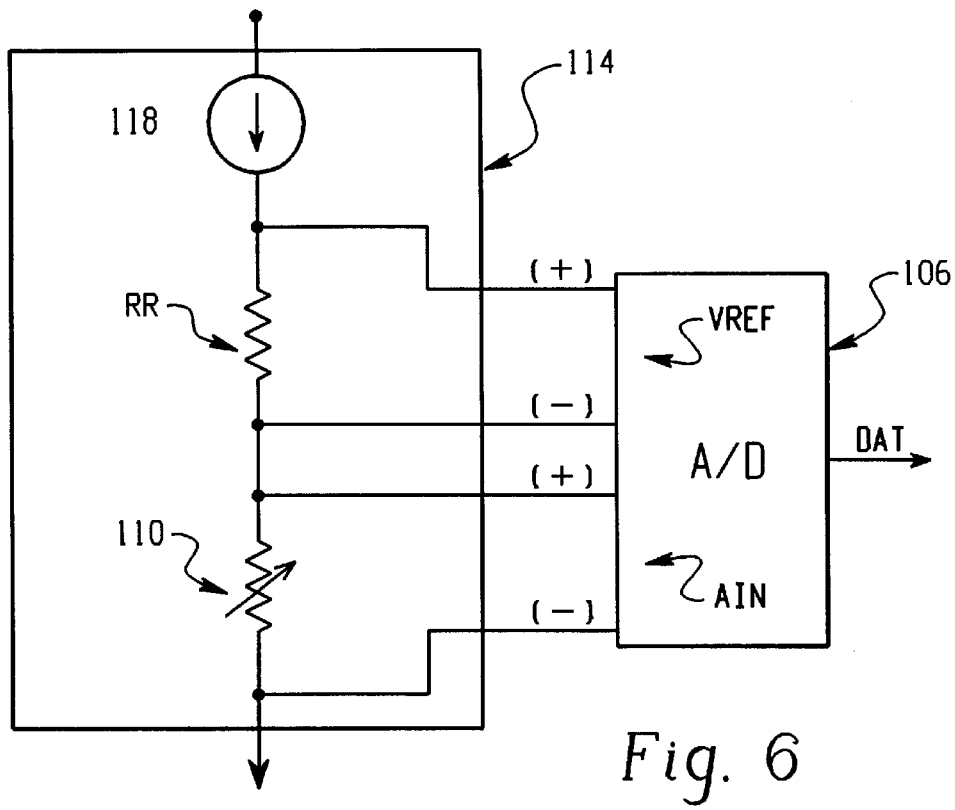
FIG. 6 schematically illustrates a ratiometric resistance temperature detector circuit in accordance with the present invention.
Figure 7:
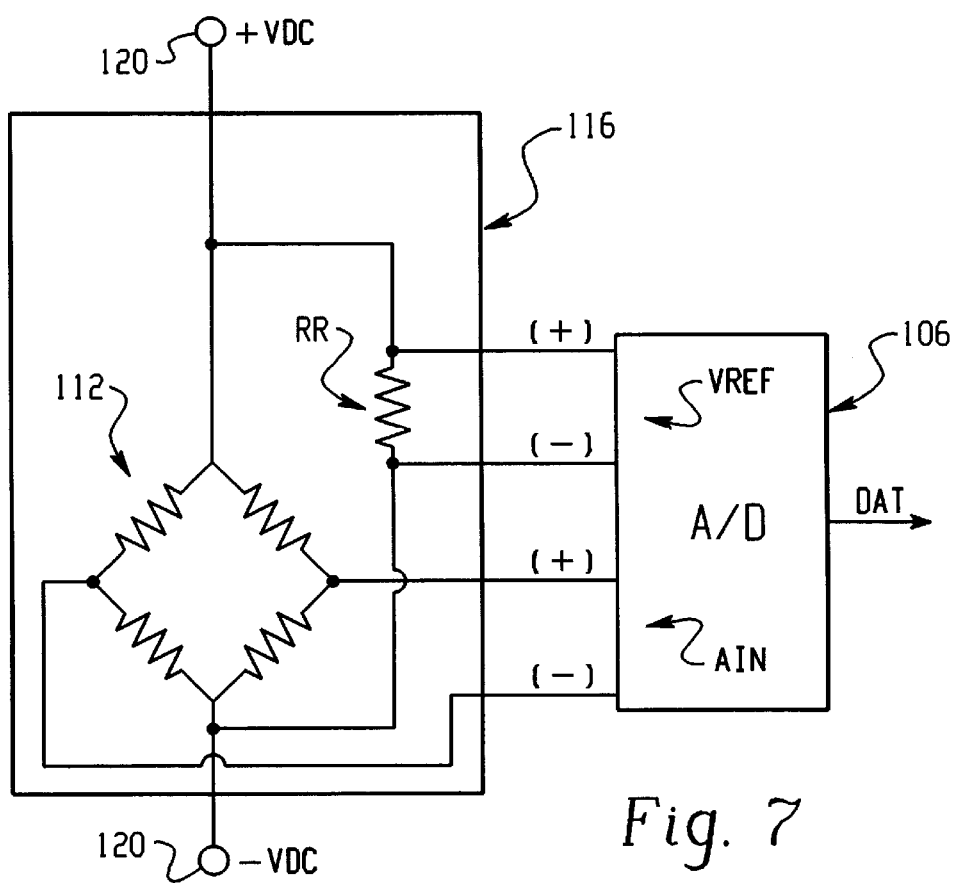
FIG. 7 schematically illustrates a ratiometric transducer circuit in accordance with the present invention.

FIGS. 6 and 7 respectively show the preferred connection of a resistance temperature detector (RTD) 110, such as the temperature sensors 100,102, and a transducer 112, such as the pressure sensors 96,98, to the analog-to-digital converter 106 to provide the ratiometric analog circuit 74. Analog-to-digital converters 106 receive a reference voltage VREF and the analog input signal AIN to produce a digital output signal DAT. In nonratiometric analog circuits, temperature changes cause the analog input signal to vary or drift without a corresponding change in the reference voltage. This causes the digital output data to change based upon the temperature of the analog circuit, even when no change in the condition being measured has actually occurred. The analog circuit 74 of the present invention selectively establishes the circuits 114,116 shown respectively in FIGS. 6 and 7 in conjunction with the analog-to-digital converter 106 to provide a ratiometric analog circuit 74.

Figure 8:
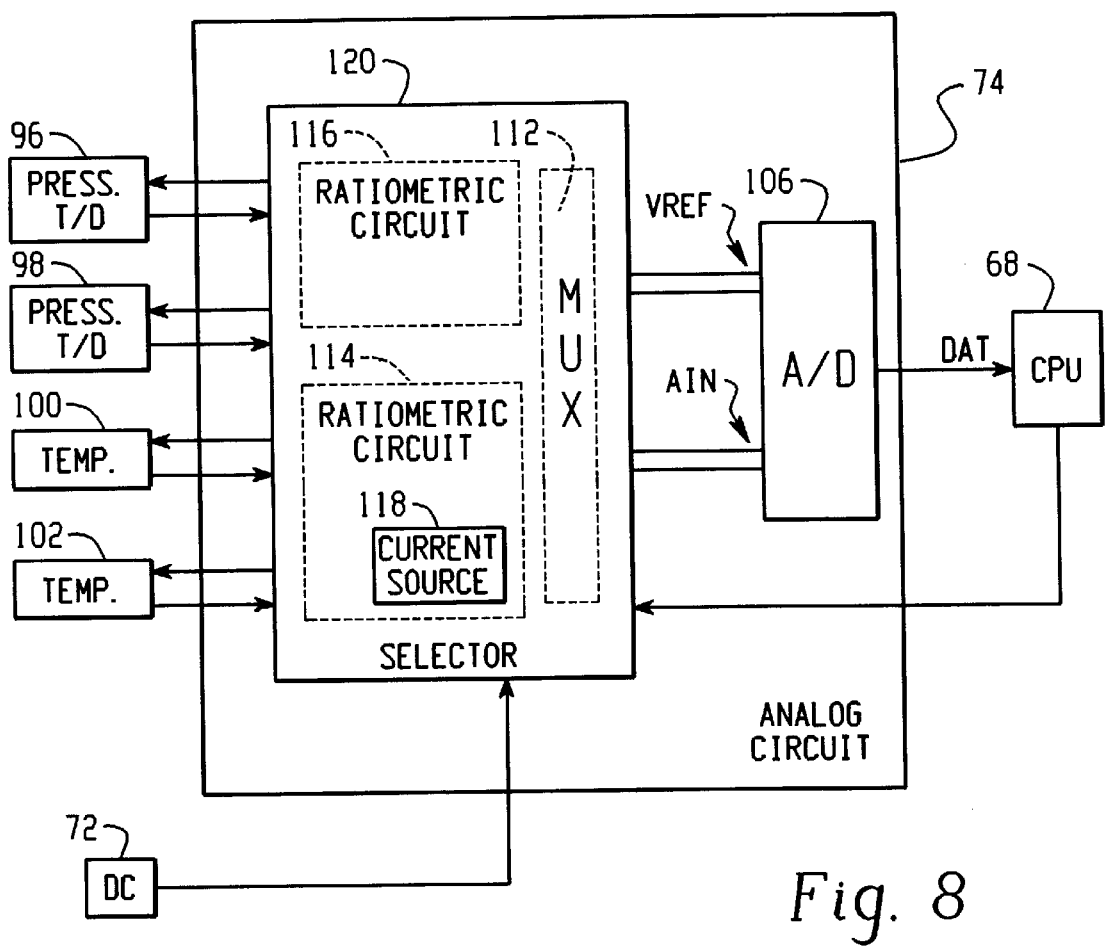
FIG. 8 schematically illustrates the analog section of the controller of FIG. 5.

With reference now also to FIG. 8, the temperature sensors 100,102 are preferably provided as RTD's 110 connected to the analog circuit 74. The pressure sensors 96,98 are preferably provided as transducers 112 connected to the circuit 74 in the manner shown in FIG. 7. The RTD 110 is connected across a current source 118 while the transducer 112 is connected across a DC voltage source 120. Both circuits 114,116 are configured such that a reference voltage VREF is obtained across a reference resistor RR. The voltages between the sensors 110,112, the circuit 74, and the reference resistor RR are all connected—any drift in one will be reflected in the other voltages. Therefore, it can be seen that as the temperature of each circuit 114,116 changes and causes a change in the analog signal AIN, the reference voltage signal VREF of each circuit 114,116 will vary in unison therewith. This allows the analog-to-digital converter 106 to accurately translate the analog signals AIN into digital data DAT. These ratiometric circuits 114,116 ensure that even in a high temperature environment of a steam sterilizer 10, the analog data AIN will be accurately converted to digital data DAT for use by the CPU 68.

As is shown in FIG. 8, the analog section 74 of the main control circuit C includes a selector circuit 120 connected to the CPU 68. In general, the selector circuit 120 allows the CPU 68 to receive data from any analog input device 96,98,100,102 connected to the analog circuit 74. When the CPU 68 requests data from one of the temperature sensors 100,102, the selector circuit 120 establishes the circuit 114 including the requested RTD sensor 100,102 and the current source 118. Likewise, when the CPU 68 requests data from one of the pressure transducers 96,98 the selector circuit 120 establishes the circuit 116 including the requested sensor 96,98. In this manner, the CPU 68 can receive data from any of the analog sensors 96,98,100,102. For example, the CPU 68 may execute a loop throughout a sterilization cycle such that each of the sensors 96,98,100,102 is sequentially selected by the selector circuit 120.

The selector circuit 120 also includes a multiplexing circuit 122 that connects a plurality of analog input devices 96,98,100,102 to the single analog-to-digital converter 106. The multiplexing circuit 122 selectively and individually connects each of the sensors 96,98,100,102 to the analog-to-digital converter 106 such that the connected sensor provides the analog input signal AIN to the analog-to-digital converter 106. The analog-to-digital converter 106 provides digital output data DAT to the CPU 68 for processing. The analog circuit 74 also includes an onboard temperature sensor (not shown) which provides the CPU 68 with data indicating the temperature of the main control circuit C.

Figure 9:
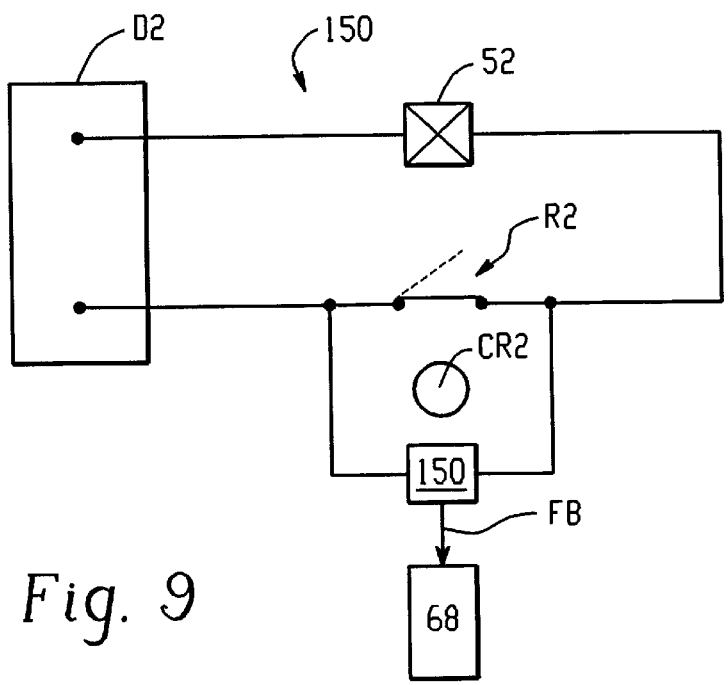
FIG. 9 schematically illustrates the switched neutral feedback circuit of the present invention.
Figure 10:
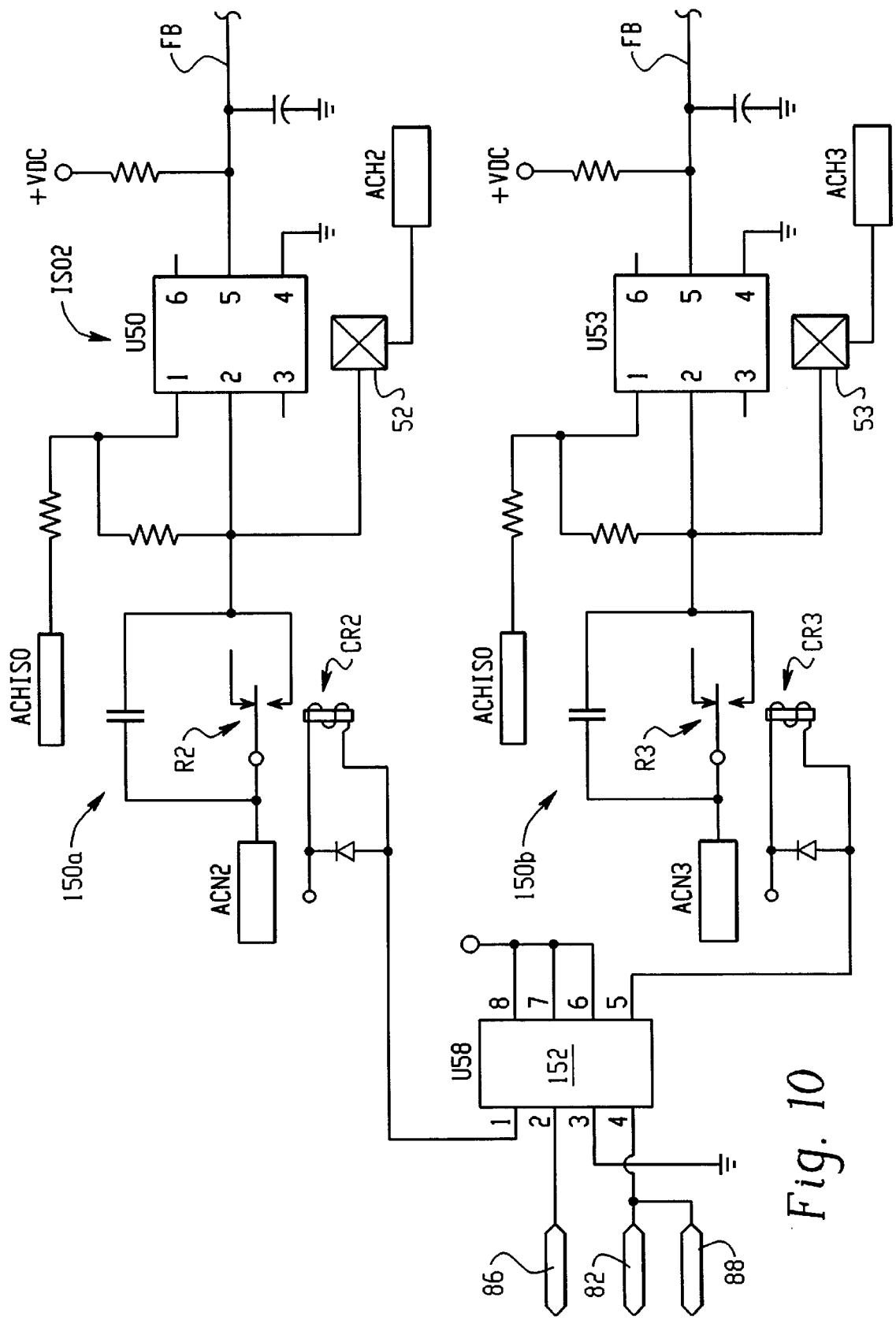
FIG. 10 is a detailed schematic illustration of a switched neutral feedback circuit in accordance with the present invention; and, FIG. 11 schematically illustrates an over-temperature feedback circuit in accordance with the present invention.

With reference now also to FIGS. 9 and 10, the switched neutral feedback circuit means of the present control system is illustrated. The switched neutral feedback circuit 150 is provided as a part of the AC output circuit 66. The feedback circuit 150 provides feedback FB to the CPU 68 that allows the CPU 68 to monitor the actual opening and closing of the relay contacts R2,R3 when a corresponding relay coil CR2, CR3 is energized or deenergized. The neutral AC power connection of both the chamber steam valve S2 and the active seal steam valve S3 is selectively completed through relays R2,R3, respectively. The relays R2,R3 are opened and closed in response to inputs from the door switch 86, the seal pressure switch 88, and the steam chamber float switch 82 to prevent the steam valves S2,S3 from being opened when the seal 42 is not intact, when the door 14 is not closed, or when water is present in the chamber 12.

With prior steam sterilizers, relays were controlled to interrupt various operations of the apparatus in response to switch inputs, but without a feedback system. Thus, with prior steam sterilizers, if the door switch indicated that the door was ajar, for example, the CPU attempted to open relay contacts that selectively connected the steam valve(s) to the chamber to close the valve(s). The CPU opened the relay contact by energizing or deenergizing the relevant relay coil. With prior systems, the CPU assumed that the relay contacts actually opened. However, it was possible that the relay failed in the closed position or that some other error occurred in the relay coil circuit that prevented the proper interruption of the steam valve circuit. This exposed an operator of the steam sterilizer to dangerously hot steam.

The AC output driver circuit 66 of the main controller circuit C implements a switched neutral feedback circuit 150 that provides feedback FB to the CPU 68 that allows the CPU 68 to monitor the actual change-of-state for the relays R2,R3 that selectively connect the neutral AC power line of each steam valve S2,S3, respectively. In this manner, a failed relay R2,R3 or relay coil CR2,CR3 will not allow hot steam to be injected into the chamber 12 when the control circuit C has attempted to interrupt the flow of steam.

Specifically, as is shown in FIG. 9 with reference to the chamber steam valve S2, the AC output driver D2 selectively provides AC power to the valve S2 in response to commands from the CPU 68 to energize and open the valve S2. When the valve S2 is energized, it opens to allow steam to be injected into the steam chamber 12. A relay R2 selectively connects the neutral AC power line to the valve S2. In response to a change-of-state in one of the switches 82,86,88, the control circuit C energizes or deenergizes the relay coil CR2 to open or close the relay R2. A switched neutral feedback circuit 150 provides feedback FB to the CPU 68 that informs the CPU 68 if the relay R2 properly opened or closed in response to the coil CR2 being energized or deenergized. The switched neutral feedback circuit 150 is preferably optically isolated from the AC power circuit of the valve S2 to protect the electronics of the control system 20.

FIG. 10 illustrates in further detail one embodiment of a switched neutral feedback circuit in accordance with the present invention. Specifically, a switched neutral feedback circuit 150*a*,150*b* is provided in association with each relay R2,R3, respectively. The switched neutral feedback circuit 150*a* allows the CPU 68 to monitor the state of the relay R2 to ensure that steam is not unintentionally injected into the chamber 12 through the steam valve S2. The switched neutral feedback circuit 150*b* operates in the same fashion as the circuit 150*a* and allows the CPU 68 to monitor the state of the relay R3 to ensure that steam is not unintentionally injected into the active seal 42 through the steam valve S3.

With continuing reference to the circuit 150*a* of FIG. 10, the valve S2 is connected to a hot AC connection ACH2. The relay R2 selectively connects the valve S2 to a neutral AC connection ACN2. The relay coil CR2 is selectively energized to close the contacts of the relay R2 and connect the valve S2 to the ACN2 connection and thus allow the valve to be energized. An optical isolator ISO2 is utilized to provide isolated feedback FB to the CPU 68 regarding the status of the relay R2. Specifically, when the relay R2 is closed, continuity is established between a hot AC connection ACHISO and the neutral ACN2 connection through pins 1 and 2 of the isolator IS02. Continuity between pins 1 and 2 at the input side of the isolator IS02 provides continuity between the pins 4 and 5 at an output side of the isolator IS02 such that the feedback connection FB changes state from +VDC volts to ground potential. The door switch 86, the chamber float switch 82 and the seal pressure switch 88 are operatively connected to the feedback circuit 150a through a driver chip 152 that energizes and deenergizes the coil CR2 depending upon the state of the input switches 82,86,88. To ensure that the relay R2 and its coil CR2 are functioning properly, the CPU 68 looks for a change in state or potential in the feedback FB whenever the driver 152 changes the state of the relay coil CR2 in response to the input switches 82,86,88. In this manner, the CPU 68 is isolated from the AC power but can monitor the status of the AC neutral connection ACN2.

The switched neutral feedback circuit 150b operates in the same fashion to monitor the state of the relay R3 provided in association with the solenoid valve S3. Those skilled in the art will recognize that although a switched neutral feedback circuit is described, the relays R2,R3 and the associated feedback circuits 150a,150b can alternatively be incorporated into the hot AC power circuits ACH2,ACH3 of each valve S2,S3. Further, the switched neutral feedback circuits 150a,150b can also be implemented with solid state rather than mechanical relays.

Figure 11:
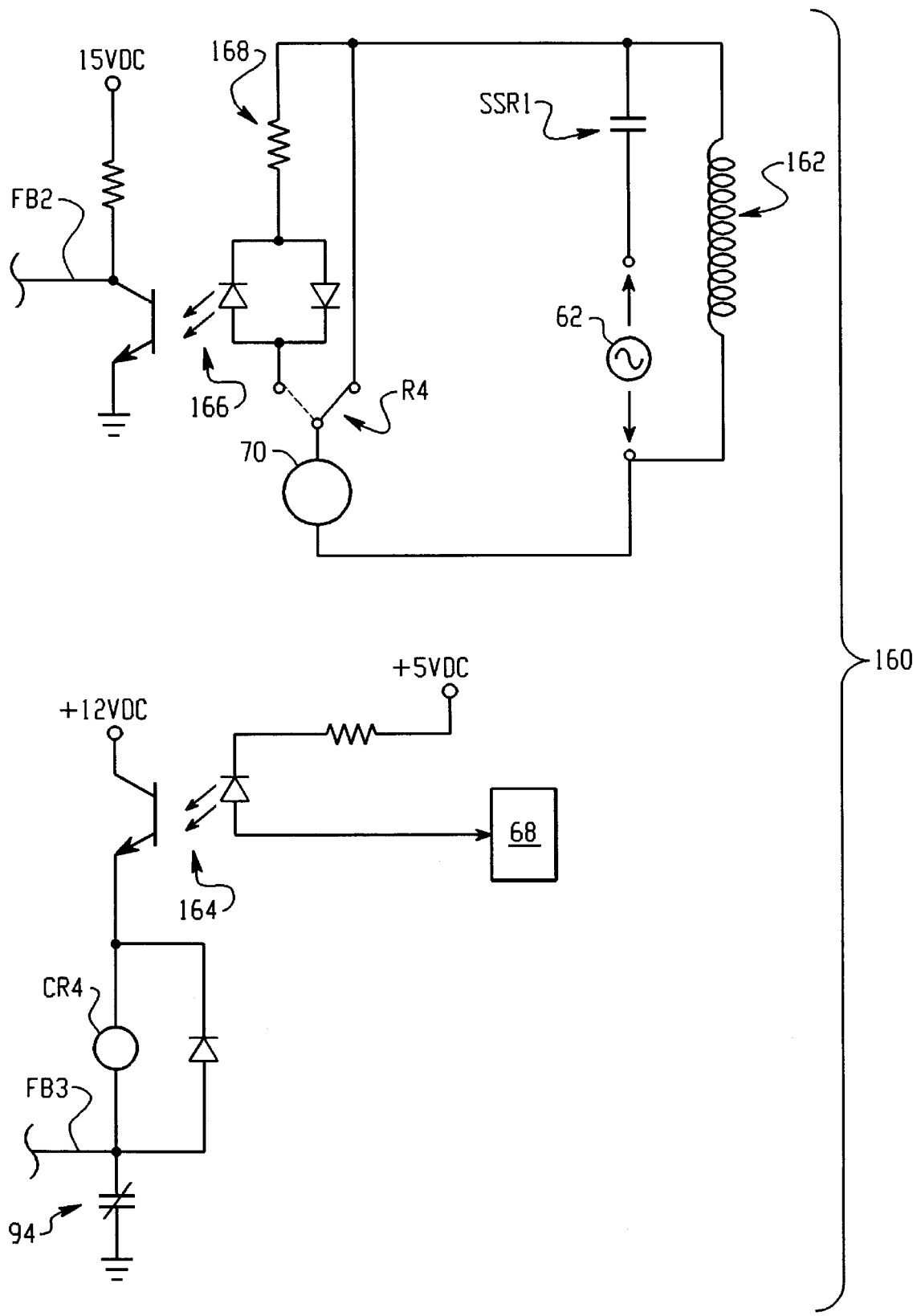

As is shown in FIG. 11, the control system further comprises an over-temperature feedback circuit 160 that monitors the temperature of the steam generation block 56 to prevent damage thereto from excessive heat. The steam generation block 56 includes a plurality of heating elements 162. The heating elements 162 are selectively connected to an AC power source 62 through a relay such as the solid state relay SSR1. A normally closed relay R4 is provided and, when closed, selectively connects the trip coil 70 of the power box 60 directly to the AC power source 62. When the relay R4 is closed, current from the source 62 will cause the trip coil 70 to interrupt the circuit and will deactivate the heating elements 162.

A relay coil CR4 is selectively energized by the CPU 68 to open the normally closed relay R4. The CPU 68 controls the flow of current through the relay coil CR4 by means of an optical isolator 164. When the CPU 68 allows current to flow through an input side of the isolator 164, current is consequently conducted through the output side of the isolator 164 and the relay coil CR4. The opening of the relay R4 causes an input of a second optical isolator 166 to conduct current. The flow of current at the input side of the second isolator 166 allows current to be conducted at the output side thereof such that the feedback connection FB2 changes state from +VDC to ground potential when the relay R4 is opened. The feedback connection FB2 is connected to the CPU 68 and provides a feedback signal to the CPU 68 when the relay R4 is opened. Also, when the relay R4 is opened, a current limiting resistor 168 limits the current to the trip coil 70 such that, under normal conditions, it does not interrupt the circuit.

To prevent overheating of the steam generation block 56, the block includes an overtemperature switch 94 which is preferably a bi-metal switch or the like. The switch 94 is normally closed and conducts current from the coil CR4 to ground. However, if the block 56 begins to overheat, as might occur if the solid state relay SSR1 fails in an "on" state, the switch 94 opens. The opening of the switch 94 interrupts the circuit energizing the coil CR4 such that the coil CR4 is deenergized. When the coil CR4 is deenergized, the relay R4 closes and the trip coil 70 is activated to interrupt the flow of current to the heating elements 162. When the switch 94 changes state as described, the CPU 68 is notified through a change-of-state in the feedback connection FB3. of course, the over-temperature feedback circuit 160 can be implemented with either mechanical or solid state relays.

The control system also preferably monitors the condition of the water filter 50 based upon the amount of time it takes for the filtered water storage tank 52 to refill after water is evacuated therefrom for a steam sterilization cycle. The apparatus 10 executes a variety of different sterilization cycles. Each type of cycle requires a select amount of steam and therefore results in the use of a select amount of water. The CPU 68 is programmed with an acceptable refill time for the tank 52 for each type of sterilization cycle. Based upon the state of the float switch 53, the CPU 68 monitors the tank refill time. A time that exceeds the preprogrammed acceptable refill time indicates a clogged filter 50. Therefore, when refill times exceed the preprogrammed limit for any given sterilizer cycle, the CPU 68 causes the display 24 or the output from the printer 28 to indicate the need for a new filter element 50.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A steam sterilizer apparatus comprising:

a steam chamber;

a steam generator having a steam output in selective fluid communication with said steam chamber, said steam generator including at least one heating element selectively connected to an electrical heating element power source; and, an electronic control system including:

a central processing unit;

an over-temperature switch positioned to sense the temperature of said steam generator; and, means for disconnecting said at least one heating element from said electrical heating element power source in response to a change of state in said over-temperature switch indicating an over-temperature condition in said steam generator; and, an over-temperature feedback circuit providing feedback to said central processing unit in response to a change of state of said over-temperature switch;

a first steam valve selectively connecting a steam output of said steam generator to said steam chamber, said first steam valve operatively connected to said electronic control system and openable and closable by said electronic control system;

a first relay selectively interconnecting said first steam valve with a source of electrical power when said contacts of said first relay are closed;

at least one water level switch for detecting the presence of excessive water in said chamber, said at least one water level switch operatively connected to a coil of said first relay to open contacts of said first relay when said at least one switch detects excessive water in the chamber of said sterilizer apparatus;

a door selectively blocking an access opening of said steam chamber;

a second steam valve selectively connecting a steam output of said steam generator to a pressure seal positioned between said door and said access opening, said second steam valve operatively connected to said electronic control system and openable and closable by said electronic control system;

a second relay selectively interconnecting said second steam valve with a source of electrical power when contacts of said second relay are closed;

at least one seal pressure switch for detecting proper pressurization of said pressure seal, said at least one seal pressure switch operatively connected to a coil of said second relay to open said contacts of said second relay when said seal is not properly pressurized; and, first and second feedback means provided respectively in association with said first and second relays, each of said first and second feedback means providing a feedback signal having a first state to said electronic controller when its respective relay is in said on state and providing a feedback signal having a second state to said electronic controller when its respective relay is in said off state.

2. The steam sterilizer apparatus as set forth in claim 1 wherein said electronic control system further comprises:

a plurality of analog sensors including at least one pressure transducer and at least one resistance temperature detector for sensing Pressure and temperature in said chamber, respectively; and, a ratiometric analog circuit including an analog-to-digital converter, said analog circuit including means for selectively individually connecting each of said plurality of analog sensors to said an analog-to-digital converter so that drift of analog signals from each of said plurality of analog sensors in response to temperature changes is compensated for by said ratiometric analog circuit.

3. A steam sterilizer apparatus comprising:

a steam chamber;

a steam generator having a steam output in selective fluid communication with said steam chamber, said steam generator including at least one heating element selectively connected to an electrical heating element power source;

an electronic control system including:
 a central processing unit,
 an over-temperature switch positioned to sense the temperature of said steam generator, and,
 means for disconnecting said at least one heating element from said electrical heating element power source in response to a change of state in said over-temperature switch indicating an over-temperature condition in said steam generator; and,
 a feedback circuit providing feedback to said central processing unit in response to a change of state of said over-temperature switch; said disconnecting means including:
  normally closed relay contacts selectively connecting said electrical heating element power source to a trip coil when said contacts are closed so that said trip coil is activated and disconnects said at least one heating element from said electrical heating element power source; and
  a relay coil for opening said relay contacts when said relay coil is energized, said over-temperature switch of said steam generator selectively deenergizing said relay coil when said over-temperature switch detects an over-temperature condition in said steam generator so that said relay closes thus activating said trip coil to interrupt electrical power to said at least one heating element.

4. The steam sterilizer apparatus as set forth in claim 2 wherein said over-temperature switch is a normally closed bi-metal switch.

5. A steam sterilizer apparatus comprising:

a steam chamber;

a steam generator having a steam output in selective fluid communication with said steam chamber, said steam generator including at least one heating element selectively connected to an electrical heating element power source;

an electronic control system including:
 a central processing unit,
 a normally closed bi-metal over-temperature switch positioned to sense the temperature of said steam generator and adapted to interrupt a first relay coil energizing circuit in response to an over-temperature condition of said steam generator, and,
 a first relay including contacts for disconnecting said at least one heating element from said electrical heating element power source in response to a change of state in said over-temperature switch indicating an over-temperature condition in said steam generator; and,
 a feedback circuit providing feedback to said central processing unit in response to a change of state of said over-temperature switch, said feedback circuit including:
  a first optical isolator having an input connected to said central processing unit and an output connected to a first relay coil associated with said first relay for energizing said first coil in response to an input from said central processing unit; and,
  a second optical isolator having an input connected to said electric heating element power source when said relay contacts of said first relay are open and an output connected to said central processing unit, said output of said second optical isolator providing feedback to said central processing unit when said relay contacts of said first relay open and close, wherein said first relay connects said electrical heating element power source to a trip coil when said contacts are closed so that said trip coil disconnects said at least one heating element from said electrical heating element power source, said over-temperature switch of said steam generator selectively deenergizing said first relay coil when said over-temperature switch detects an over-temperature condition in said steam generator so that said contacts of said first relay close.

6. A steam sterilizer comprising:

a steam chamber;

a steam generator having a steam output in selective fluid communication with said steam chamber, said steam generator including at least one heating element selectively connected to an electrical heating element power source; and, an electronic control system including:

a central processing unit;

an over-temperature switch positioned to sense the temperature of said steam generator;

means for disconnecting said at least one heating element from said electrical heating element power source in response to a change of state in said over-temperature switch indicating an over-temperature condition in said steam generator; and, a feedback circuit providing feedback to said central processing unit in response to a change of state of said over-temperature switch;

a first steam valve selectively connecting a steam output of said steam generator to said steam chamber, said first steam valve operatively connected to said electronic control system and openable and closable by said electronic control system;

a first relay selectively interconnecting said first steam valve with a source of electrical power when said contacts of said first relay are closed;

at least one switch for detecting an error condition, said at least one switch operatively connected to a coil of said first relay to open contacts of said first relay when said at least one switch detects an error condition of said sterilizer apparatus;

a door selectively blocking an access opening of said steam chamber;

a second steam valve selectively connecting a steam output of said steam generator to a pressure seal positioned between said door and said access opening, said second steam valve operatively connected to said electronic control system and openable and closable by said electronic control system;

a second relay selectively interconnecting said second steam valve with a source of electrical power when contacts of said second relay are closed;

at least one switch for detecting an error condition, said at least one switch operatively connected to a coil of said second relay to open said contacts of said second relay when said at least one switch detects an error condition of said sterilizer apparatus.

7. The steam sterilizer apparatus as set forth in claim 6, wherein said at least one switch detects an error condition including at least one of a door open error condition, a defective door seal error condition, and a liquid accumulation in the steam chamber error condition.

8. The steam sterilizer apparatus as set forth in claim 6, further comprising first and second optical isolators operatively and respectively connected to said first and second relays, said first and second optical isolators respectively providing isolated feedback to said central processing unit from said first and second relays.

9. A sterilizer/disinfector apparatus comprising:

a generally hollow steam chamber;

a door providing selective access to said steam chamber;

a steam generator;

a first steam valve selectively connecting an output of said steam generator with said steam chamber;

a second steam valve selectively communicating steam to a door seal;

first and second relays provided, respectively, in association with said first and second steam valves, each of said first and second relays controllable by an electronic controller between an on state and an off state, said off state of each of said first and second relays, respectively, disconnecting said first and second steam valves from a source of electrical power to close said first and second valves; and, first and second feedback circuits in association with said first and second relays, each of said first and second feedback circuits providing a feedback signal having a first state to said electronic controller when its respective relay is in said on state and providing a feedback signal having a second state to said electronic controller when its respective relay is in said off state.

10. The sterilizer/disinfector as set forth in claim 9, wherein said first and second feedback circuits respectively comprise first and second optical isolators providing isolated electrical feedback signals to said electronic controller.

11. A steam comprising:

a generally hollow steam chamber;

a door providing selective access to said steam chamber;

a heated steam generation block including at least one electric heating element for generating steam;

at least one steam valve selectively connecting an output of said steam generation block in fluid communication with at least said steam chamber;

an electronic controller operatively connected to said at least one steam valve for opening and closing said at least one steam valve;

a heating element relay selectively interconnecting said at least one heating element to a source of electrical power;

an over-temperature switch sensing the temperature of said steam generation block; and, means for selectively disconnecting said at least one heating element from said source of electrical power when said over-temperature switch detects an over-temperature condition of said steam generation block.

12. The steam apparatus as set forth in claim 11 wherein said disconnecting means comprises an over-temperature relay selectively energizing a heating circuit trip coil, said over-temperature switch operatively connected to a coil associated with said over-temperature relay such that said over-temperature relay energizes said trip coil when said over-temperature switch detects an over-temperature condition of said steam generation block.

13. A sterilizer/disinfector apparatus comprising:

a generally hollow steam chamber;

a door providing selective access to said steam chamber;

means for generating steam;

at least one steam valve selectively connecting an output of said steam generating means in fluid communication with at least said steam chamber;

an electronic controller operatively connected to said at least one steam valve for opening and closing said at least one steam valve;

at least one analog sensor sensing at least one of a temperature condition and a pressure condition within said generally hollow steam chamber;

an analog input circuit including an analog-to-digital converter connected to receive analog input signals from said at least one analog sensor and to send digital data to said electronic controller, said analog input circuit including means for establishing a ratiometric circuit including said at least one analog sensor, said ratiometric circuit compensating for temperature-induced drift of said analog input signals from said at least one analog sensor to said analog-to-digital converter.

14. The sterilizer/disinfector apparatus as set forth in claim 13 further comprising.
   at least one resistance temperature detector for measuring temperature in said chamber;
   at least one transducer for measuring pressure in said chamber;
   a selector circuit for selecting one of a ratiometric resistance temperature detector circuit and a ratiometric transducer circuit respectively including said at least one resistance temperature detector and said pressure transducer; and,
   a multiplexing circuit for selectively connecting one of said ratiometric circuits to an input of said analog-todigital converter.

15. An apparatus for sterilizing or disinfecting medical devices comprising:
   a generally hollow steam chamber adapted to receive medical devices therein;
   at least one analog pressure sensor for sensing pressure in said chamber;
   at least one analog temperature sensor for sensing temperature in said chamber; and,
   an analog input circuit including:
     an analog-to-digital converter;
     a ratiometric input circuit including one of said temperature and pressure sensors, said ratiometric circuit compensating for temperature-induced drift of signals from said temperature and pressure sensors; and
     a multiplexing circuit for selectively connecting each of said ratiometric input circuits to an input of said analog-to-digital converter.

16. The apparatus for sterilizing or disinfecting medical devices as recited in claim 15, further comprising:
   means for generating steam;
   a normally closed valve selectively connecting an output of said steam generation means to said chamber;
   an electronic controller selectively energizing said valve from a source of electrical power to open said valve;
   at least one relay selectively connecting said valve means to said source of electrical power;
   at least one switch detecting an error condition, said at least one switch operatively connected to said relay such that said valve is disconnected from said source of electrical power and closed when said at least one switch detects an error.

17. The apparatus for sterilizing or disinfecting medical devices as recited in claim 16, further comprising:
   feedback means connected to said at least one relay and providing feedback to said electronic controller regarding the state of said at least one relay.

* * * * *